US012183179B2

(12) United States Patent
Uchiyama et al.

(10) Patent No.: US 12,183,179 B2
(45) Date of Patent: Dec. 31, 2024

(54) SPATIAL MONITORING SYSTEM

(71) Applicant: ZeroOne Inc., Hamamatsu (JP)

(72) Inventors: Takashi Uchiyama, Hamamatsu (JP);
Shuji Niihara, Hamamatsu (JP);
Kazuya Natsume, Shinshiro (JP)

(73) Assignee: ZeroOne Inc. (JP)

( * ) Notice: Subject to any disclaimer, the term of this patent is extended or adjusted under 35 U.S.C. 154(b) by 60 days.

(21) Appl. No.: 18/001,209

(22) PCT Filed: Jan. 25, 2022

(86) PCT No.: PCT/JP2022/002634
§ 371 (c)(1),
(2) Date: Dec. 8, 2022

(87) PCT Pub. No.: WO2022/176526
PCT Pub. Date: Aug. 25, 2022

(65) Prior Publication Data
US 2023/0215263 A1 Jul. 6, 2023

(30) Foreign Application Priority Data
Feb. 17, 2021 (JP) .................. 2021-022975

(51) Int. Cl.
*G08B 21/12* (2006.01)
*G01D 21/02* (2006.01)
*G16H 50/80* (2018.01)

(52) U.S. Cl.
CPC ............. *G08B 21/12* (2013.01); *G01D 21/02* (2013.01); *G16H 50/80* (2018.01)

(58) Field of Classification Search
CPC ......... G08B 21/12; G01D 21/02; G16H 50/80
See application file for complete search history.

(56) References Cited

U.S. PATENT DOCUMENTS

| 11,531,311 B2 * | 12/2022 | Matsumoto | .............. F24F 11/74 |
| 2019/0122759 A1 * | 4/2019 | Wakimoto | ............ G16H 40/20 |
| 2022/0102007 A1 * | 3/2022 | Palanivel | ............... G08B 21/02 |

FOREIGN PATENT DOCUMENTS

| CN | 110497420 A | * 11/2019 | ............. B25J 11/00 |
| JP | 2019079136 A | 5/2019 | |

(Continued)

OTHER PUBLICATIONS

Cresco Digital Technologies Inc., Industry-academia joint research with Creative Japan and the University of Electro-Communications solves the "Three Cs"! "CLIP New Corona Infection Prevention Support System" that supports the optimal number of people in the space and ventilation, Aug. 27, 2020, 9 pages (Year: 2020).*

(Continued)

*Primary Examiner* — Curtis A Kuntz
*Assistant Examiner* — James E Munion
(74) *Attorney, Agent, or Firm* — Endurance Law Group PLC; James R. Yee

(57) ABSTRACT

A space monitoring system includes environment measuring means for measuring an atmospheric environment of a monitored space (S), person sensing means for sensing the existence of a person in the monitored space (S), space condition calculating means for calculating whether the monitored space is an indoor environment likely to cause droplet infection or whether the monitored space is expected to become an indoor environment likely to cause droplet infection, based on atmospheric environment data measured by the environment measuring means and person data sensed by the person sensing means, and display means for displaying an indication for facilitating a user to improve an existing indoor environment likely to cause droplet infection or prevent the monitored space from becoming an indoor environment likely to cause droplet infection, based on a (Continued)

result of calculation by the space condition calculating means.

14 Claims, 9 Drawing Sheets

(56) References Cited

FOREIGN PATENT DOCUMENTS

| | | | |
|---|---|---|---|
| JP | 2020135486 A | 8/2020 | |
| KR | 20130119707 A | 11/2013 | |
| WO | 2019044254 A1 | 3/2019 | |
| WO | WO-2021207775 A1 * | 10/2021 | .............. F24F 11/30 |

OTHER PUBLICATIONS

Cresco Digital Technologies Inc., Industry-academia joint research with Creative Japan and the University of Electro-Communications solves the "Three Cs"! "CLIP New Corona Infection Prevention Support System" that supports the optimal number of people in the space and ventilation, Aug. 27, 2020, 9 pages.

Japanese Decision of Refusal and English Translation for JP Patent Application No. 2023-500668, dated Sep. 26, 2024, 6 pages.

\* cited by examiner

SPATIAL MONITORING SYSTEM

CROSS REFERENCE TO RELATED APPLICATIONS

This application is a national stage application of WO PCT/JP2022/002634 filed on Jan. 25, 2022, which claims priority to Japanese Patent Application JP 2021-022975 filed on Feb. 17, 2021, the entire disclosures of which are hereby incorporated by reference and relied upon.

TECHNICAL FIELD

The present disclosure relates to a space monitoring system that monitors the condition of an indoor monitored space and displays the condition.

BACKGROUND ART

Some systems have been proposed for monitoring the conditions of indoor monitored spaces and displaying the conditions. For example, Patent Literature 1 discloses a vacant room management device and a multipurpose toilet. This vacant room management device includes storage means for storing vacancy information on a private room, receiving means for receiving a door open/close detection signal indicating detection of opening or closing of a door of the private room from opening/closing detecting means for detecting opening or closing and a human existence detection signal indicating detection of the human existence from human existence detecting means for detecting the human existence in the private room, and updating means for updating the vacancy information. The updating means updates the vacancy information to information indicating full occupancy in response to reception of the human existence detection signal, and updates the vacancy information to information indicating vacancy in response to reception of the door open/close detection signal.

CITATION LIST

Patent Literature

Patent Literature 1: Unexamined Japanese Patent Application Publication No. 2020-135486

SUMMARY OF INVENTION

Technical Problem

Unfortunately, the existing systems for monitoring the conditions of indoor monitored spaces and displaying the conditions like that disclosed in Patent Literature 1 are just responsible for monitoring and lack a specific mechanism for facilitating some actions, often resulting in no subsequent action of a user.

An objective of the present disclosure, which has been accomplished in view of this situation, is to provide a space monitoring system that can monitor the condition of an indoor monitored space and then motivate a user to take an action for infection control, for example, refrain from entering the monitored space or ventilate the monitored space.

Solution to Problem

A space monitoring system according to a first aspect of the present disclosure includes: environment measuring means for measuring an atmospheric environment of the monitored space; person sensing means for sensing the existence of a person in the monitored space; space condition calculating means for calculating whether the monitored space is an indoor environment likely to cause droplet infection or whether the monitored space is expected to become an indoor environment likely to cause droplet infection, based on atmospheric environment data measured by the environment measuring means and person data sensed by the person sensing means; and display means for displaying an indication for facilitating a user to improve an existing indoor environment likely to cause droplet infection or prevent the monitored space from becoming an indoor environment likely to cause droplet infection, based on a result of calculation by the space condition calculating means.

In a space monitoring system according to a second aspect of the present disclosure, the display means displays the person data or an environmental condition that is based on the atmospheric environment data, on a floor-plan image of the monitored space.

In a space monitoring system according to a third aspect of the present disclosure, the display means displays a three-dimensional image of at least one of a shape of the monitored space or the person data.

In a space monitoring system according to a fourth aspect of the present disclosure, the display means displays a three-dimensional image of at least one of a shape of the monitored space or an environmental condition that is based on the atmospheric environment data.

In a space monitoring system according to a fifth aspect of the present disclosure, the display means displays an indication for facilitating the user to improve the existing indoor environment likely to cause droplet infection and/or prevent the monitored space from becoming an indoor environment likely to cause droplet infection, by means of characters, symbols, and/or colors.

In a space monitoring system according to a sixth aspect of the present disclosure, the atmospheric environment of the monitored space measured by the environment measuring means is at least one of a temperature, a humidity, an atmospheric pressure, a carbon dioxide concentration, a carbon monoxide concentration, an oxygen concentration, a content of volatile organic compounds, an amount of dust, an amount of pollen, or an amount of fine particulate matters.

In a space monitoring system according to a seventh aspect of the present disclosure, the space condition calculating means causes artificial intelligence to calculate whether the monitored space is an indoor environment likely to cause droplet infection.

Advantageous Effects of Invention

The space monitoring system according to the present disclosure can monitor the condition of an indoor monitored space and then motivate a user to take an action for infection control, for example, refrain from entering the monitored space or ventilate the monitored space.

DESCRIPTION OF EMBODIMENTS

Figure 1:
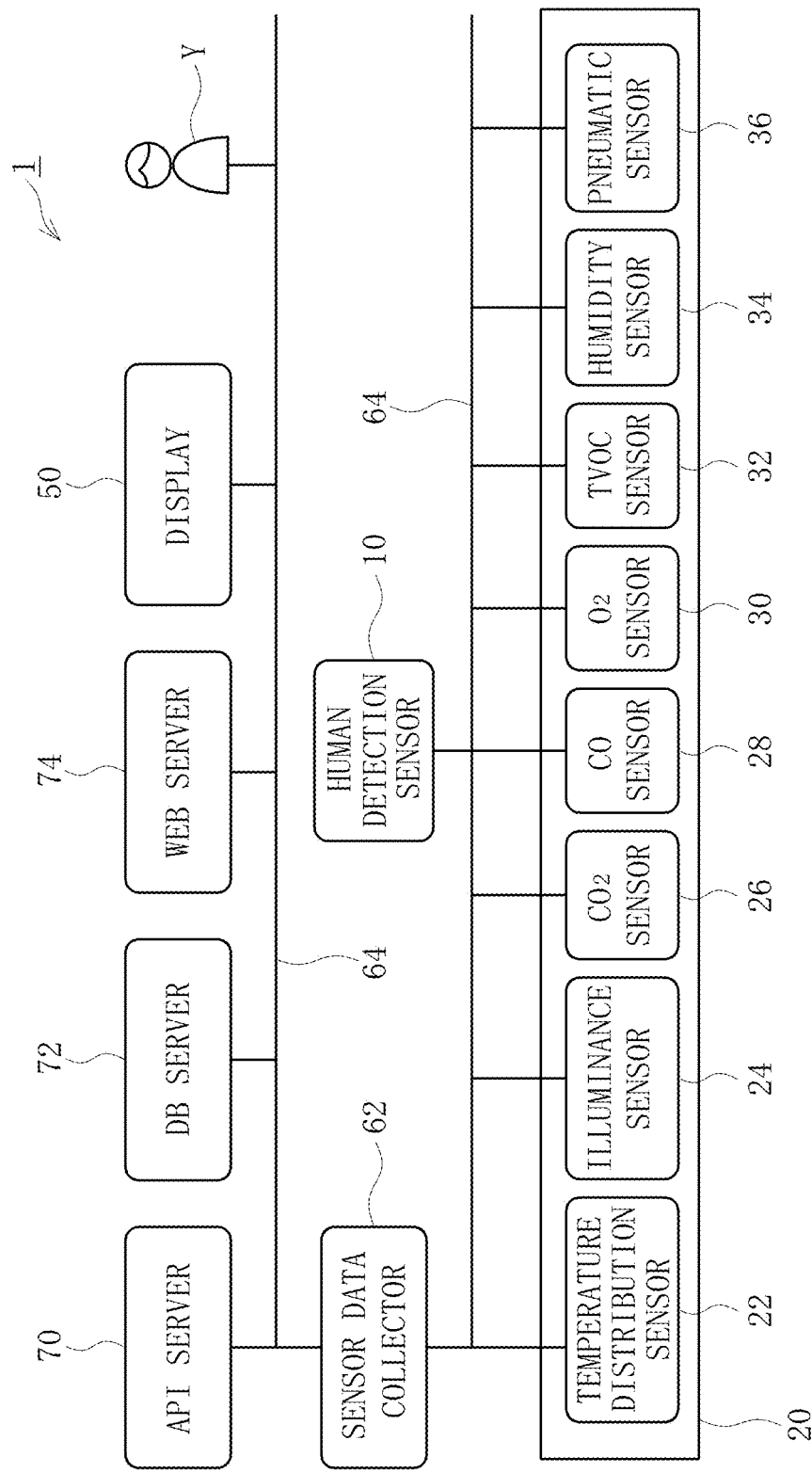
FIG. 1 illustrates an exemplary configuration of a space monitoring system according to the present disclosure.
Figure 2:
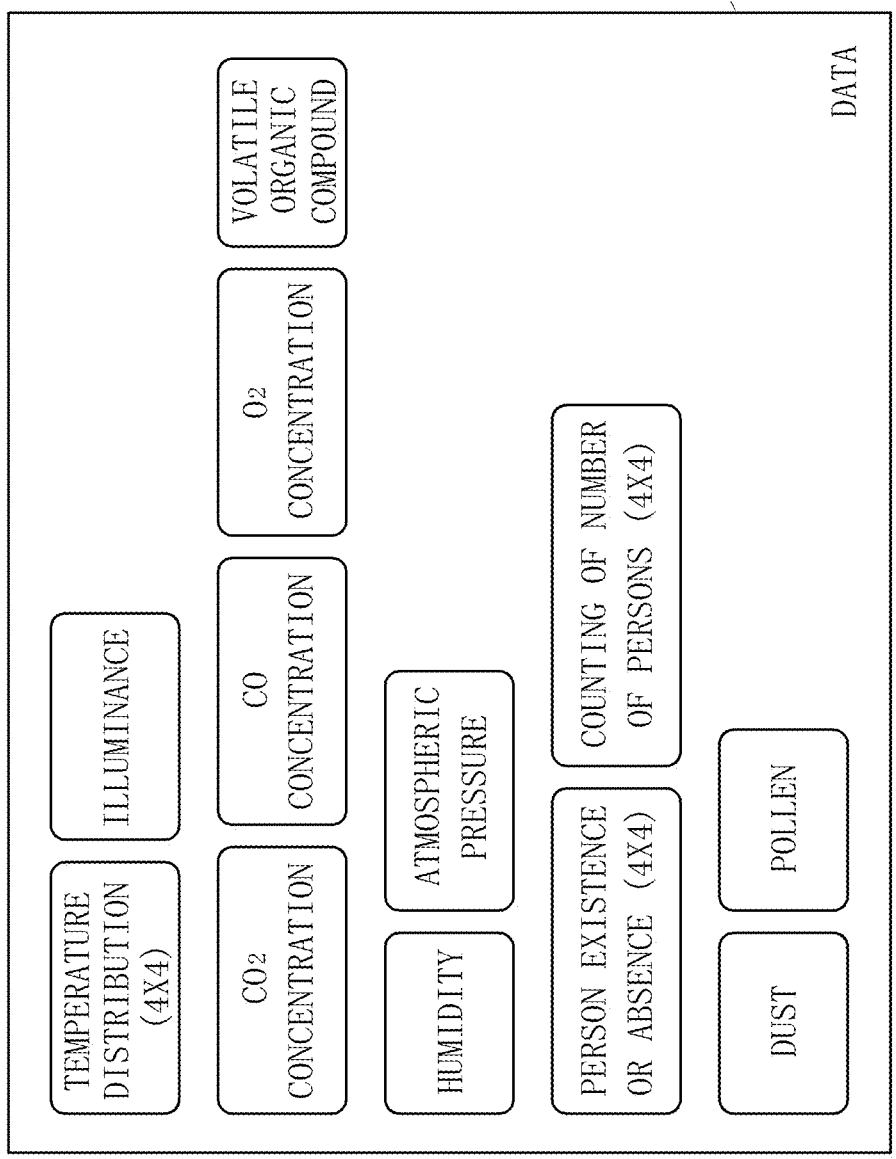
FIG. 2 is an explanatory diagram illustrating exemplary data managed in the space monitoring system.
Figure 3:
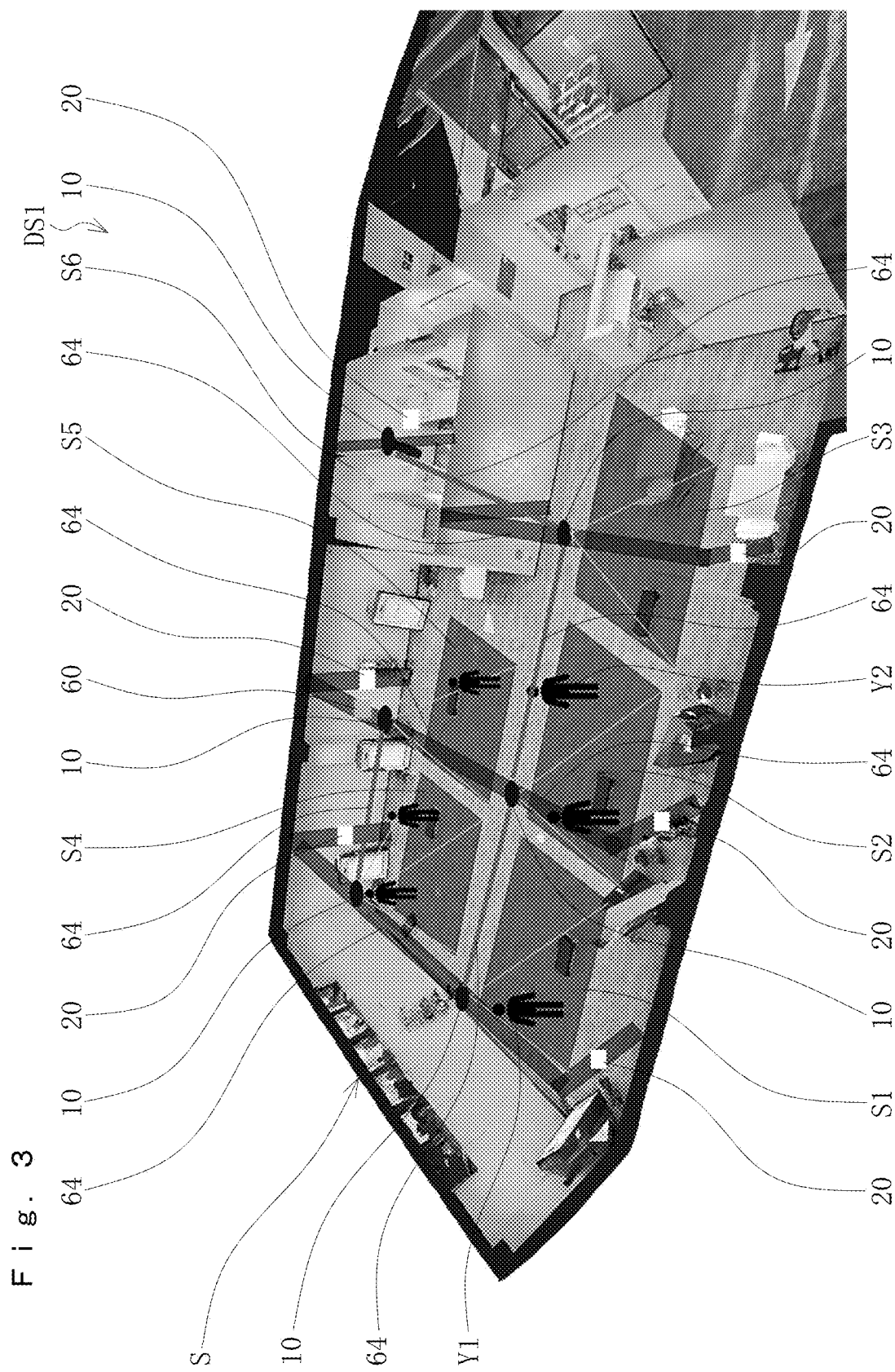
FIG. 3 is an explanatory diagram illustrating an exemplary three-dimensional image in the space monitoring system.
Figure 4:
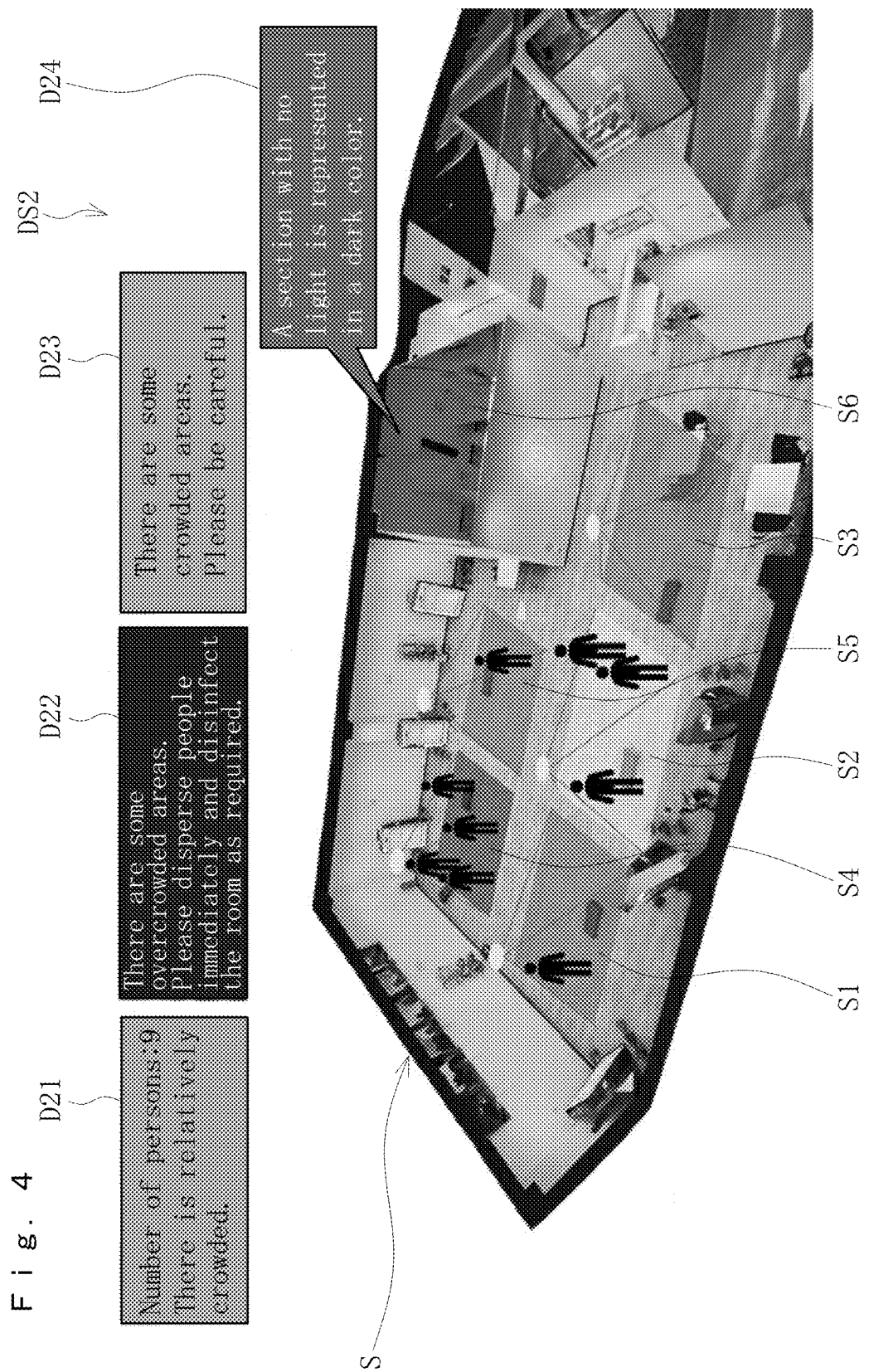
FIG. 4 is an explanatory diagram illustrating exemplary indications including characters and the like in a three-dimensional image in the space monitoring system.
Figure 5:
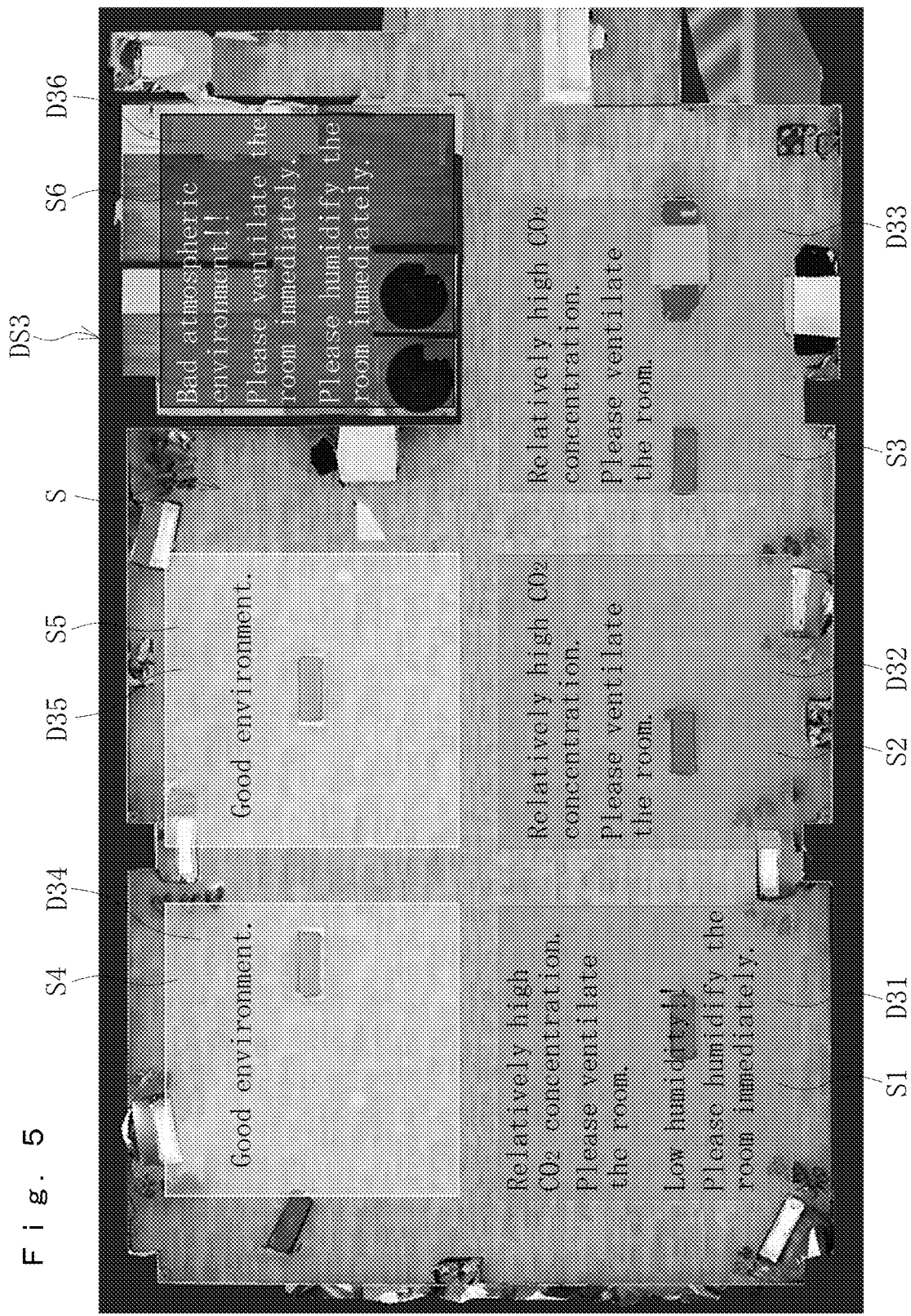
FIG. 5 is an explanatory diagram illustrating exemplary indications including characters and the like in a floor-plan image in the space monitoring system.
Figure 6:
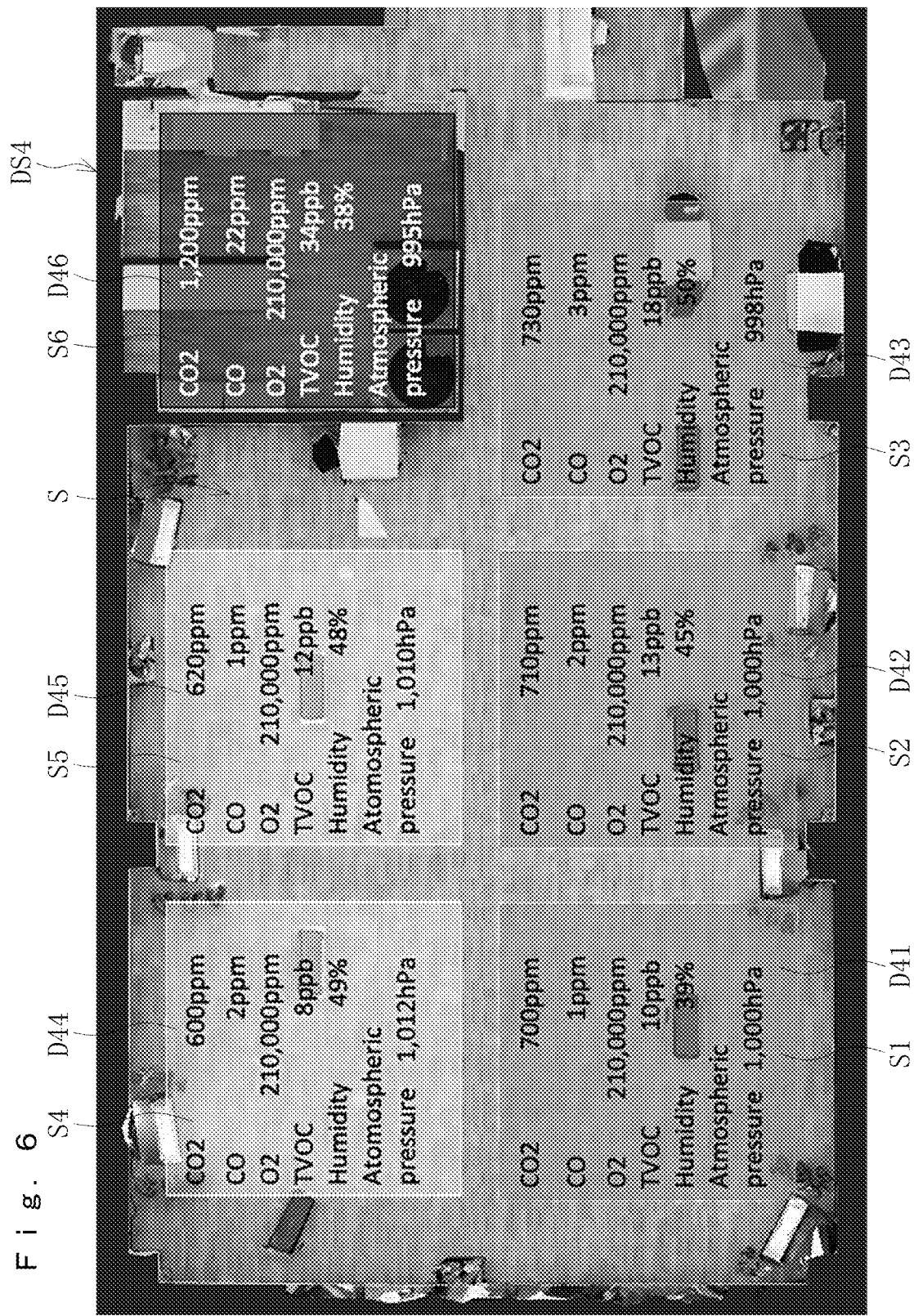
FIG. 6 is an explanatory diagram illustrating exemplary indications including values and the like in a floor-plan image in the space monitoring system.
Figure 7:
FIG. 7 is an explanatory diagram illustrating an exemplary screen in another space monitoring system.
Figure 8:
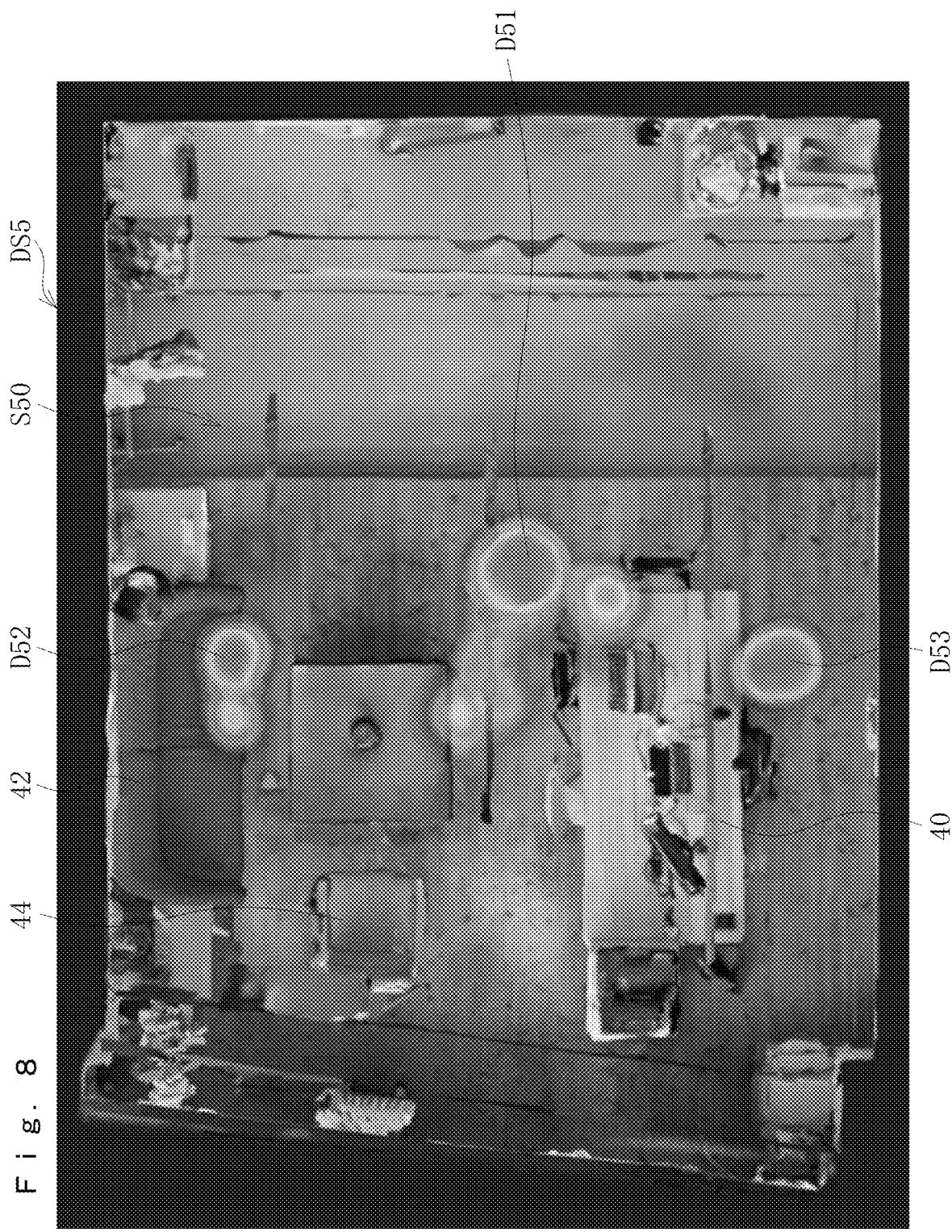
FIG. 8 is an explanatory diagram illustrating a change in the screen in the space monitoring system illustrated in FIG. 7.
Figure 9:
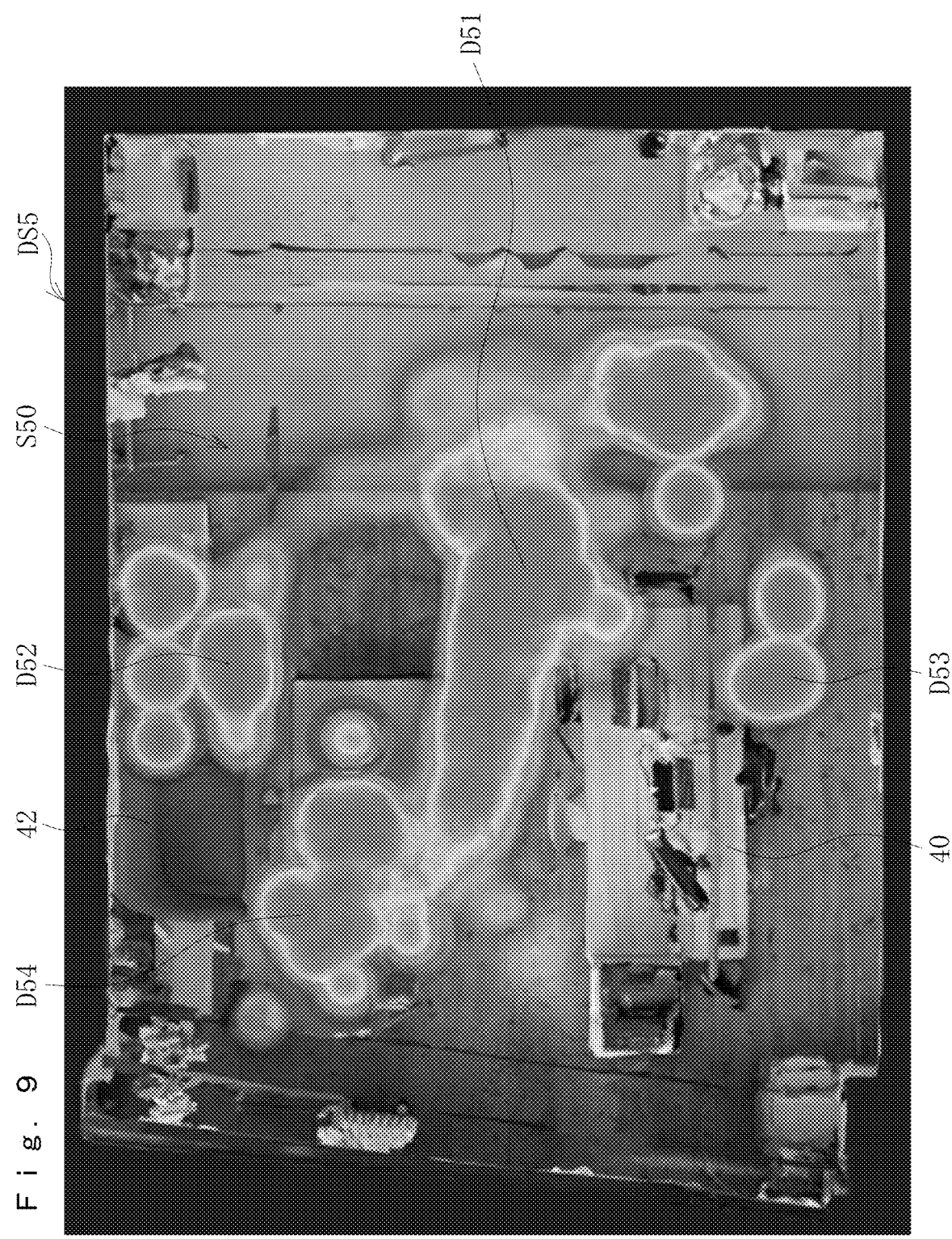
FIG. 9 is an explanatory diagram illustrating a further change in the screen in the space monitoring system illustrated in FIG. 7.

An embodiment of the present disclosure is specifically described with reference to the accompanying drawings. FIG. 1 illustrates an exemplary configuration of a space monitoring system according to the present disclosure. FIG. 2 is an explanatory diagram illustrating exemplary data managed in the space monitoring system. FIG. 3 is an explanatory diagram illustrating an exemplary three-dimensional image in the space monitoring system. FIG. 4 is an explanatory diagram illustrating exemplary indications including characters and the like in a three-dimensional image in the space monitoring system. FIG. 5 is an explanatory diagram illustrating exemplary indications including characters and the like in a floor-plan image in the space monitoring system. FIG. 6 is an explanatory diagram illustrating exemplary indications including values and the like in a floor-plan image in the space monitoring system. FIG. 7 is an explanatory diagram illustrating an exemplary screen in another space monitoring system. FIG. 8 is an explanatory diagram illustrating a change in the screen in the space monitoring system illustrated in FIG. 7. FIG. 9 is an explanatory diagram illustrating a further change in the screen in the space monitoring system illustrated in FIG. 7.

A space monitoring system 1 according to the present disclosure is an apparatus that monitors the condition of a monitored space S that is located indoors and displays the condition. As illustrated in FIG. 1 and other figures, the space monitoring system 1 has a hardware configuration including a controller 60 made of an electronic computer, air quality sensors 20, a human detection sensor 10, and a display 50, for example.

The controller 60 is designed to perform functions of the space monitoring system 1 for comprehensive control of various types of means (hardware and software), which are described below. The display 50 serves as a monitor of the controller 60 and also as display means, which is described below, for performing a function of the space monitoring system 1. The controller 60 includes or is connected to components, such as the display 50, a sensor data collector 62, an API server 70, a database (DB) server 72, a WEB server 74, the human detection sensor 10, and the air quality sensors 20. The connection between the controller 60 and the components may have any configuration. A typical example is a LAN connection via a LAN network 64 (the LAN connection is not necessarily a wired connection and may be a wireless connection).

The entire space monitoring system 1, the WEB server 74, and the API server 70 are connected to the outside of the system via a telecommunication network. This external connection may use a wired network (for example, metal network or optical network) or a wireless network, and these communication networks are mere examples.

FIG. 1 illustrates a person Y as if the person Y is also electrically connected to the space monitoring system 1. This illustration means that a portable information terminal, such as smartphone, is connected to the space monitoring system 1 via a wired or wireless network, and the person Y having this portable information terminal is assumed to have direct connection to the space monitoring system 1. The portable information terminal owned by the person Y is connected to the space monitoring system 1 and can thereby perform the functions of the display 50. In order to allow the portable information terminal to perform the functions of the display 50, the portable information terminal may use some functions of the space monitoring system 1 from the outside by means of the API server 70, the portable information terminal may be connected via the WEB server 74 by a browsing method, or the portable information terminal may be directly connected via a LAN to the controller 60 as a monitor, for example.

The air quality sensors 20 are made of one or more sensors and serve as environment measuring means for measuring an atmospheric environment of the monitored space S and measuring atmospheric environment data. The air quality sensors 20 are configured as a collection of a temperature distribution sensor 22, an illuminance sensor 24, a carbon dioxide concentration sensor (CO2 sensor) 26, a carbon monoxide concentration sensor (CO sensor) 28, an oxygen concentration sensor (O2 sensor) 30, a total volatile organic compound (TVOC) sensor 32, a humidity sensor 34, and a pneumatic sensor 36, for example. Actually, some of these functions are physically performed by a single sensor.

The temperature distribution sensor 22 measures a temperature distribution within the area covered by the sensor. The illuminance sensor 24 measures an illuminance within the area covered by the sensor. The carbon dioxide concentration sensor (CO2 sensor) 26 measures a carbon dioxide concentration in the air within the area covered by the sensor. The carbon monoxide concentration sensor (CO sensor) 28 measures a carbon monoxide concentration in the air within the area covered by the sensor. The oxygen concentration sensor (O2 sensor) 30 measures an oxygen concentration in the air within the area covered by the sensor. The TVOC sensor 32 measures a concentration of total volatile organic compounds in the air within the area covered by the sensor, that is, a level of contamination of various volatile organic compounds (VOCs). The humidity sensor 34 measures a humidity in the air within the area covered by the sensor. The pneumatic sensor 36 measures an atmospheric pressure within the area covered by the sensor.

The environment measuring means may also measure at least one of an amount of dust, an amount of pollen, or an amount of fine particulate matters (for example, amount of PM2.5), in addition to the temperature, the humidity, the atmospheric pressure, the carbon dioxide concentration, the carbon monoxide concentration, the oxygen concentration, or the content of volatile organic compounds.

The human detection sensor 10 serves as person sensing means for sensing the existence of a person Y within the monitored space S, and sensing person data, such as the existence or absence of persons (person existence or absence) and counting of the number of persons, within the area covered by the human detection sensor 10. The human detection sensor 10 may be an infrared sensor or a semiconductor laser (LiDAR sensor) in terms of hardware, but these sensors are mere examples.

FIG. 2 illustrates exemplary data managed in the sensor data collector 62. Examples of the atmospheric environment data 68 include a temperature, an illuminance, a carbon dioxide concentration, a carbon monoxide concentration, an oxygen concentration, a content of volatile organic compounds, an amount of dust, an amount of pollen, a humidity, and an atmospheric pressure. Examples of the person data include the existence or absence of persons (person existence or absence) and counting of the number of persons. The sensor data collector 62 collects and accumulates the measured data.

An arrangement of the various types of means in the actual monitored space S is described below with reference to the drawings. The monitored space S illustrated in FIG. 3 and other figures is an indoor space like a hall, for example, where unspecified persons enter and exit by which convection occurs the indoor space. The space monitoring system 1 is designed to monitor the condition of this monitored space S. The monitored space S itself may be used for any purpose and have various applications, such as restaurant and pub.

The monitored space S has a certain area, and thus is divided into six sections (sections S1 to S6) for measurement/sensing, grasp, and display in this embodiment. A single monitored space may be divided or not divided for measurement/sensing, grasp, and display, and the condition whether the monitored space is divided is not to be construed as limiting the present disclosure.

The monitored space S is provided with at least one controller 60. The controller 60 is connected to other devices installed in the monitored space S via the LAN network 64 (the other devices are also connected to each other in the same manner). The individual devices are connected via a telecommunication network (Internet) to a public network or other network outside the monitored space S as required. In the example illustrated in FIG. 3, the sensor data collector 62 is integrated with the controller 60. The display 50 in this embodiment is not an independent monitor but a portable information terminal owned by the person Y. That is, screens DS1 to DS4 illustrated in FIGS. 3 to 6 are displayed on the portable information terminal.

Each of the sections S1 to S6 of the monitored space S is provided with the human detection sensor 10 on the ceiling. Each of the sections S1 to S6 is also provided with the air quality sensors 20 on a wall.

The following description is directed to operations of the space monitoring system 1 having the above-described configuration. As a basic operation of the space monitoring system 1, the controller 60 first serves as space condition calculating means to calculate whether the monitored space S is an indoor environment likely to cause droplet infection or whether the monitored space S is expected to become an indoor environment likely to cause droplet infection, based on the atmospheric environment data measured by the air quality sensors 20, which serve as the environment measuring means, and the person data sensed by the human detection sensor 10, which serves as the person sensing means. Conceivable specific examples of the infection include diseases, such as coronavirus disease 2019 (COVID-19) and influenza virus acute infection, which are caused or likely to be caused through spreading of droplets from a patient, but these infectious virus diseases are mere examples.

The display 50 then displays indications for facilitating a user to improve the existing indoor environment likely to cause droplet infection or prevent the monitored space S from becoming an indoor environment likely to cause droplet infection, based on the result of calculation by the controller 60, which serves as the space condition calculating means.

Specifically, the space condition calculating means executes calculation based on the relationship between the humidity and temperature in the air and the number of persons Y in the monitored space S, the condition whether the air has a high carbon dioxide concentration and requires ventilation, and the crowd level of persons Y, such as an extremely large number of persons Y, for example. The specific calculation by the space condition calculating means involves calculation, based on the person data, of a crowd level of persons Y and grasp, based on the atmospheric environment data, of an environmental condition, for example. The person data and the environmental condition when displayed also function as indications for facilitating the user to improve the existing indoor environment likely to cause droplet infection or prevent the monitored space S from becoming an indoor environment likely to cause droplet infection.

The indications for facilitating the user to improve the existing indoor environment likely to cause droplet infection or prevent the monitored space S from becoming an indoor environment likely to cause droplet infection displayed on the display 50 are described below with reference to FIGS. 3 to 6.

The screen DS1 illustrated in FIG. 3 is an exemplary screen displayed on the display 50. The screen DS1 in FIG. 3 contains a three-dimensional image of the shape of the monitored space S and a crowd level of persons Y1 and Y2 (person data) displayed on the display 50. The persons Y1 and Y2 are also represented to have three-dimensional appearances as well as the shape of the monitored space S. The persons Y1 and Y2 in the screen DS1 are not three-dimensional at a glance, and may also be expressed in completely three-dimensional patterns.

The display 50 displays the three-dimensional image of the monitored space S based on the actual floor plan and thus achieves representation on a floor-plan image. The floor-plan image may be line drawing, photograph, or graphic, and may be a two-dimensional or three-dimensional expression, and these expressions are mere examples. The display 50 is able to display the monitored space S while shifting the viewpoint to any angle. The individual sections S1 to S6 are provided with different colors, to allow the user to objectively recognize the number of persons Y1 and Y2 existing in each of the sections S1 to S6, visually confirm the crowd level of persons Y1 and Y2, and find whether the monitored space S is an indoor environment likely to cause droplet infection. The screen DS1 can therefore facilitate the user to improve the existing indoor environment likely to cause droplet infection or prevent the monitored space S from becoming an indoor environment likely to cause droplet infection.

In the screen DS1 in FIG. 3, the crowd level of persons Y1 and Y2 may be directly expressed using images of the persons Y1 and Y2 or expressed in different colors provided to the floor surfaces of the sections S1 to S6, for example, and these expressions are mere examples.

The presentation of the shape of the monitored space S allows the user to imagine air flows and movements of persons in the monitored space S, thereby achieving a three-dimensional representation of the environmental condition when combined with the atmospheric environment data. The environmental condition is not necessarily expressed in a three-dimensional image and may be expressed in a two-dimensional image.

FIG. 4 illustrates the screen DS2, which is an exemplary screen displayed on the display 50. The screen DS2 contains a three-dimensional image of the shape of the monitored space S and a crowd level of persons (person data) displayed on the display 50, like the screen DS1. The image of a crowd level of persons (person data) is not necessarily a three-dimensional image and may also be a two-dimensional image.

The screen DS2 contains, in addition to the three-dimensional image in the screen DS1, characters and colors (grayscale intensities in the figures) for facilitating the user to improve the existing indoor environment likely to cause droplet infection or prevent the monitored space S from becoming an indoor environment likely to cause droplet infection.

Specifically, the individual floor surfaces of the sections S1 to S5 are provided with different colors (grayscale intensities in the figures) to represent the respective crowd levels of persons depending on the conditions of the sections S1 to S6. The colors of the floor surfaces may also represent the quality levels of atmospheric environment as well as the specific crowd levels of persons. The section S6 where the light is turned off is expressed in a dark color to indirectly suggest no overcrowding. The display 50 can therefore achieve indications for facilitating the user to improve the existing indoor environment likely to cause droplet infection or prevent the monitored space S from becoming an indoor environment likely to cause droplet infection.

The screen DS2 contains indications (indications D21, D22, D23, and D24) for facilitating the user to improve the existing indoor environment likely to cause droplet infection and/or prevent the monitored space S from becoming an indoor environment likely to cause droplet infection, and displays the indications, in addition to the three-dimensional image, using different colors (grayscale intensities in the figures) for the characters and the backgrounds of the characters. The indications for facilitating an action of the user may include symbols and patterns, and these indications are mere examples. That is, the screen DS2 is an exemplary screen including both of a three-dimensional image and a two-dimensional image.

FIG. 5 illustrates the screen DS3, which is an exemplary screen displayed on the display 50. The screen DS3 includes a floor-plan image of the shape of the monitored space S and a crowd level of persons displayed on the display 50.

The screen DS3 contains indications (indications D31, D32, D33, D34, D35, and D36) for facilitating the user to improve the existing indoor environment likely to cause droplet infection or prevent the monitored space S from becoming an indoor environment likely to cause droplet infection, and expresses the indications by means of the characters and colors (grayscale intensities in the figures), that is, indicates the indications using the characters and displays the indications using different colors (grayscale intensities in the figures) for the characters and the backgrounds of the characters. The indications for facilitating an actions of the user may include symbols and patterns, and these indications are mere examples.

FIG. 6 illustrates the screen DS4, which is an exemplary screen displayed on the display 50. The screen DS4 includes a floor-plan image of the shape of the monitored space S and a crowd level of persons displayed on the display 50.

The screen DS4 contains indications (indications D41, D42, D43, D44, D45, and D46) for facilitating the user to improve the existing indoor environment likely to cause droplet infection or prevent the monitored space S from becoming an indoor environment likely to cause droplet infection, and expresses the indications by means of the characters and colors (grayscale intensities in the figures), that is, indicates the values of atmospheric environment data using the characters and displays the indications using different colors (grayscale intensities in the figures) for the characters and the backgrounds of the characters.

The colors (including grayscale intensities) of images of the sections and the colors (including grayscale intensities) of images of persons in each screen can be varied in accordance with the change in the condition of the monitored space S, in order to facilitate the user to improve the existing indoor environment likely to cause droplet infection or prevent the monitored space S from becoming an indoor environment likely to cause droplet infection. For example, the residence times of the persons Y1 and Y2 may be measured and the persons Y1 and Y2 may be expressed in different colors depending on the lengths of the residence times.

Alternatively, the space condition calculating means of the space monitoring system 1 may cause artificial intelligence to calculate whether the monitored space S is an indoor environment likely to cause droplet infection. Specifically, the artificial intelligence may generate or select appropriate indications for facilitating the user to improve the existing indoor environment likely to cause droplet infection or prevent the monitored space S from becoming an indoor environment likely to cause droplet infection based on the big data and the data measured by the air quality sensors 20, and cause the indications to be displayed on the display 50.

Alternatively, the calculation and display may be conducted using a heat map, in order to facilitate the user to improve the existing indoor environment likely to cause droplet infection or prevent the monitored space from becoming an indoor environment likely to cause droplet infection. The heat map represents the intensities of numerical matrix data in colors for visualization of the data. The heat map can visualize the crowd levels of persons (person data) and the values related to the environmental condition, for example, using grayscale intensities, like a temperature distribution measured by thermography.

Specifically, the screen DS5 illustrated in FIGS. 7 to 9 represents a crowd level of persons (or an environmental condition, such as carbon dioxide concentration) in the form of a heat map. A monitored space S50 is an indoor space in which a desk 40, a sofa 42, and a chair 44 are installed. The screen DS5 illustrated in FIG. 7 does not contain indications for facilitating the user to improve the existing indoor environment likely to cause droplet infection or prevent the monitored space S50 from becoming an indoor environment likely to cause droplet infection. FIGS. 8 and 9 illustrate indications D51 to D54, which represent the existence or traveling of persons in the corresponding regions and function as indications for facilitating the user to improve the existing indoor environment likely to cause droplet infection or prevent the monitored space S50 from becoming an indoor environment likely to cause droplet infection. The areas and the grayscale intensities of the indications D51 to D54 indicate likelihoods of occurrence of droplet infection.

For example, when a person enters the monitored space S50 in FIG. 7 and starts moving, the indications D51 to D53 represented in grayscale intensities emerge as illustrated in FIG. 8. In response to entrance of another person or activation of movements of the person in the monitored space S50, the areas of the indications D51 to D53 become larger and the new indication D54 emerges as illustrated in FIG. 9.

Close observation of the screen DS5 reveals that, for example, the indications D51 to D53 around the desk 40 and the sofa 42 are small in FIG. 8, which indicate relatively low crowd levels of persons. In FIG. 9, however, the new indication D54 emerges around the chair 44 in addition to those around the desk 40 and the sofa 42, and the indications D51 to D53 become larger. These indications are deemed to have a higher level of facilitation of the user to improve the existing indoor environment likely to cause droplet infection or prevent the monitored space S50 from becoming an indoor environment likely to cause droplet infection. The indications D51 to D54 thus function as indications for facilitating the user to improve the existing indoor environment likely to cause droplet infection or prevent the monitored space S50 from becoming an indoor environment likely to cause droplet infection.

The above-described space monitoring system 1 can monitor the condition of the monitored space S or S50 and then motivate the user to take an action for infection control, for example, refrain from entering the monitored space S or S50 or ventilate the monitored space S or S50.

The space monitoring system 1 according to the present disclosure is designed as anti-infection measures. However, not limiting to the purpose of preventing infection spreading, the space monitoring system 1 may also be used for other purposes. For example, the space monitoring system 1 may be applied for the use other than anti-infection measures for the purpose of facilitating the user to avoid overcrowding from the viewpoint of disaster prevention.

This application claims the benefit of Japanese Patent Application No. 2021-022975, filed on Feb. 17, 2021, the entire disclosure of which is incorporated by reference herein.

The foregoing describes some example embodiments for explanatory purposes. Although the foregoing discussion has presented specific embodiments, persons skilled in the art will recognize that changes may be made in form and detail without departing from the broader spirit and scope of the invention. Accordingly, the specification and drawings are to be regarded in an illustrative rather than a restrictive sense. This detailed description, therefore, is not to be taken in a limiting sense, and the scope of the invention is defined only by the included claims, along with the full range of equivalents to which such claims are entitled.

INDUSTRIAL APPLICABILITY

As described above, the present disclosure can provide a space monitoring system that can monitor the condition of an indoor monitored space and then motivate a user to take an action for infection control, for example, refrain from entering the monitored space or ventilate the monitored space.

REFERENCE SIGNS LIST

1 Space monitoring system
10 Human detection sensor
20 Air quality sensor
22 Temperature distribution sensor
24 Illuminance sensor
26 Carbon dioxide concentration sensor
28 Carbon monoxide concentration sensor
30 Oxygen concentration sensor
32 TVOC sensor
34 Humidity sensor
36 Pneumatic sensor
40 Desk
42 Sofa
44 Chair
50 Display
60 Controller
62 Sensor data collector
64 LAN network
68 Atmospheric environment data
70 API server
72 DB server
74 WEB server

The invention claimed is:

1. A space monitoring system to monitor a condition of a monitored space that is located indoors and display the condition, the space monitoring system comprising:
a plurality of air quality sensors configured to measure an atmospheric environment of the monitored space;
a human detection sensor configured to sense existence of a person in the monitored space;
a controller configured to calculate whether the monitored space is an indoor environment likely to cause droplet infection or whether the monitored space is expected to become an indoor environment likely to cause droplet infection, based on atmospheric environment data measured by the plurality of air quality sensors and person data sensed by the human detection sensor; and
a display configured to display an indication for facilitating a user to improve an existing indoor environment likely to cause droplet infection or prevent the monitored space from becoming an indoor environment likely to cause droplet infection and to display a procedure for facilitating the user to improve an existing indoor environment likely to cause droplet infection or prevent the monitored space from becoming an indoor environment likely to cause droplet infection, based on a result of calculation by the controller, wherein the procedure displayed by the display includes instructions to disperse people.

2. A space monitoring system to monitor a condition of a monitored space that is located indoors and display the condition, the space monitoring system comprising:
a plurality of air quality sensors configured to measure an atmospheric environment of the monitored space;
a human detection sensor for sensing existence of a person in the monitored space;
a controller configured to calculate whether the monitored space is an indoor environment likely to cause droplet infection or whether the monitored space is expected to become an indoor environment likely to cause droplet infection, based on atmospheric environment data measured by the plurality of air quality sensors and person data sensed by the human detection sensor; and
a display configured to display an indication for facilitating a user to improve an existing indoor environment likely to cause droplet infection or prevent the monitored space from becoming an indoor environment likely to cause droplet infection and to display a procedure for facilitating the user to improve an existing indoor environment likely to cause droplet infection or prevent the monitored space from becoming an indoor environment likely to cause droplet infection, based on a result of calculation by the controller, wherein the display displays the person data or an environmental condition that is based on the atmospheric environment data, on a floor-plan image of the monitored space, wherein the procedure displayed by the display includes instructions to disperse people.

3. The space monitoring system according to claim 1, wherein the display displays a three-dimensional image of at least one of a shape of the monitored space or the person data.

4. The space monitoring system according to claim 1, wherein the display displays a three-dimensional image of at least one of a shape of the monitored space or an environmental condition that is based on the atmospheric environment data.

5. The space monitoring system according to claim 1, wherein the display displays an indication for facilitating the user to improve the existing indoor environment likely to cause droplet infection and/or prevent the monitored space from becoming an indoor environment likely to cause droplet infection, using characters, symbols, and/or colors.

6. The space monitoring system according to claim 1, wherein the atmospheric environment of the monitored space measured by the plurality of air quality sensors is at least one of a temperature, a humidity, an atmospheric pressure, a carbon dioxide concentration, a carbon monoxide concentration, an oxygen concentration, a content of volatile organic compounds, an amount of dust, an amount of pollen, or an amount of fine particulate matters.

7. The space monitoring system according to claim 1, wherein the controller causes artificial intelligence to calculate whether the monitored space is an indoor environment likely to cause droplet infection.

8. The space monitoring system according to claim 2, wherein the display displays a three-dimensional image of at least one of a shape of the monitored space or the person data.

9. The space monitoring system according to claim 2, wherein the display displays a three-dimensional image of at least one of a shape of the monitored space or an environmental condition that is based on the atmospheric environment data.

10. The space monitoring system according to claim 2, wherein the display displays an indication for facilitating the user to improve the existing indoor environment likely to cause droplet infection and/or prevent the monitored space from becoming an indoor environment likely to cause droplet infection, using characters, symbols, and/or colors.

11. The space monitoring system according to claim 2, wherein the atmospheric environment of the monitored space measured by the plurality of air quality sensors is at least one of a temperature, a humidity, an atmospheric pressure, a carbon dioxide concentration, a carbon monoxide concentration, an oxygen concentration, a content of volatile organic compounds, an amount of dust, an amount of pollen, or an amount of fine particulate matters.

12. The space monitoring system according to claim 2, wherein the controller causes artificial intelligence to calculate whether the monitored space is an indoor environment likely to cause droplet infection.

13. The space monitoring system according to claim 1, wherein the procedure displayed by the display further includes instructions to perform one or more of: ventilate, disinfect and humidify.

14. The space monitoring system according to claim 2, wherein the procedure displayed by the display further includes instructions to perform one or more of: ventilate, disinfect and humidify.

* * * * *